United States Patent [19]

DeVries

[11] Patent Number: 4,794,922

[45] Date of Patent: Jan. 3, 1989

[54] VENTILATOR MANIFOLD

[75] Inventor: Douglas F. DeVries, Redlands, Calif.

[73] Assignee: Bird Products Corporation, Riverside, Calif.

[21] Appl. No.: 927,250

[22] Filed: Nov. 4, 1986

[51] Int. Cl.$^4$ .................. A61M 16/00; A62B 7/00
[52] U.S. Cl. ............................................. 128/204.18
[58] Field of Search ............... 128/205.24, 204.23, 128/204.21, 204.18; 137/884; 74/606

[56] References Cited

U.S. PATENT DOCUMENTS

| 2,408,136 | 9/1946 | Fox | 128/204.25 |
|---|---|---|---|
| 3,191,596 | 6/1965 | Bird et al. | 128/204.19 |
| 3,646,963 | 3/1972 | Klee | 137/884 |
| 3,814,126 | 6/1974 | Klee | 137/884 |
| 3,861,385 | 1/1975 | Carden | 128/205.24 |
| 3,881,513 | 5/1975 | Chang | 137/844 |
| 3,938,551 | 2/1976 | Henkin | 137/613 |
| 4,080,103 | 3/1978 | Bird | 128/204.18 |
| 4,352,532 | 10/1982 | Hardin | 137/844 |
| 4,458,841 | 7/1984 | Laakaniemi et al. | 137/884 |
| 4,499,789 | 2/1985 | Kuramochi et al. | 74/606 |
| 4,507,707 | 3/1985 | Willis | 137/884 |
| 4,549,248 | 10/1985 | Stoll | 137/884 |

Primary Examiner—Kyle L. Howell
Assistant Examiner—Timothy G. Philips
Attorney, Agent, or Firm—Knobbe, Martens Olson & Bear

[57] ABSTRACT

A ventilator for providing artificial respiration to a patient has a plurality of pneumatic components mounted on a manifold. The manifold is a one piece aluminum casting having a base with ducts formed therein to permit fluid communication between the pneumatic components. The ducts are exposed on the underside of the base and are removably sealed from the atmosphere by a gasket and sealing plate which are secured to the underside of the base so as to cover the exposed portion of the ducts. Several components are formed in the manifold as part of the casting, including an accumulator and pulsation dampener, both of which are gas storage chambers. A plurality of fins are also formed as part of the manifold, and act as a heat sink for a printed circuit board which is secured to the manifold. Removable pneumatic components are secured to mounting blocks which extend upwardly from the base and have threaded bores therein for the receipt of threaded fasteners. Fluid communication between the ducts and the pneumatic components is established through stubs which extend upwardly from the base and which are sealingly engaged by the pneumatic components. A bore through the stubs forms an access port to the ducts. The access ports as aligned with inlets and outlets on the pneumatic components when the pneumatic components are secured to the mounting blocks.

22 Claims, 3 Drawing Sheets

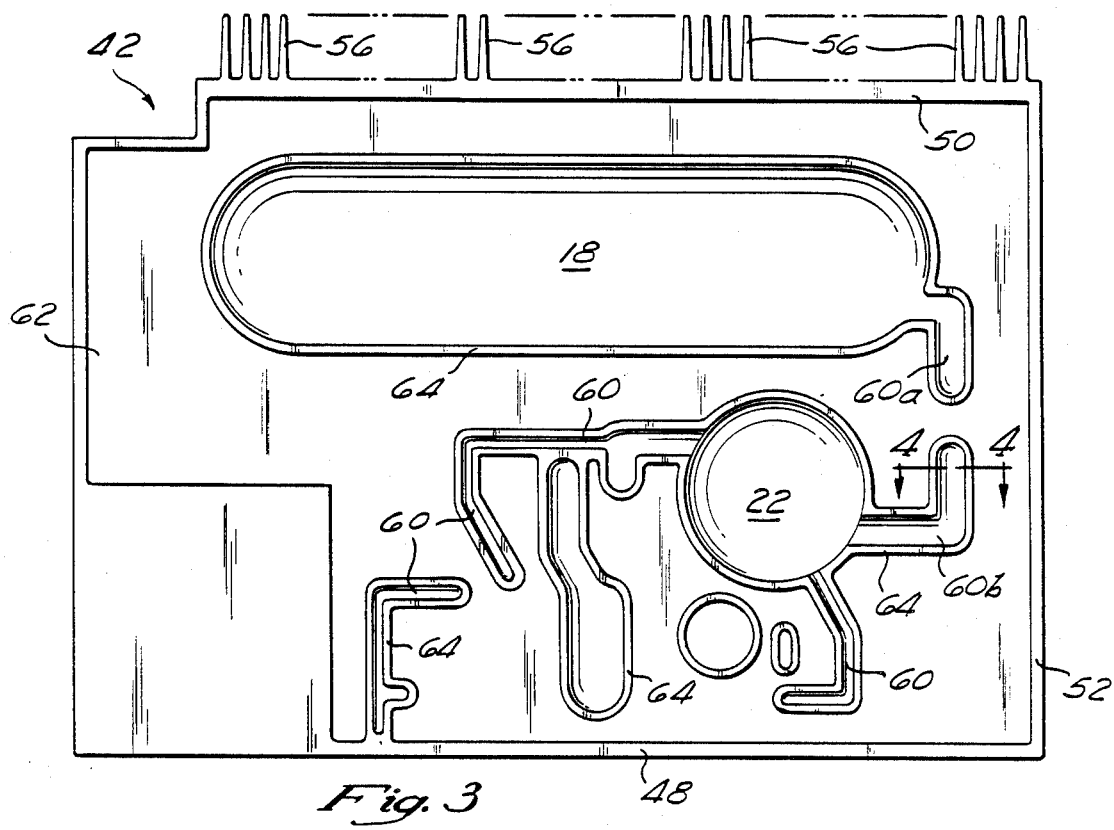
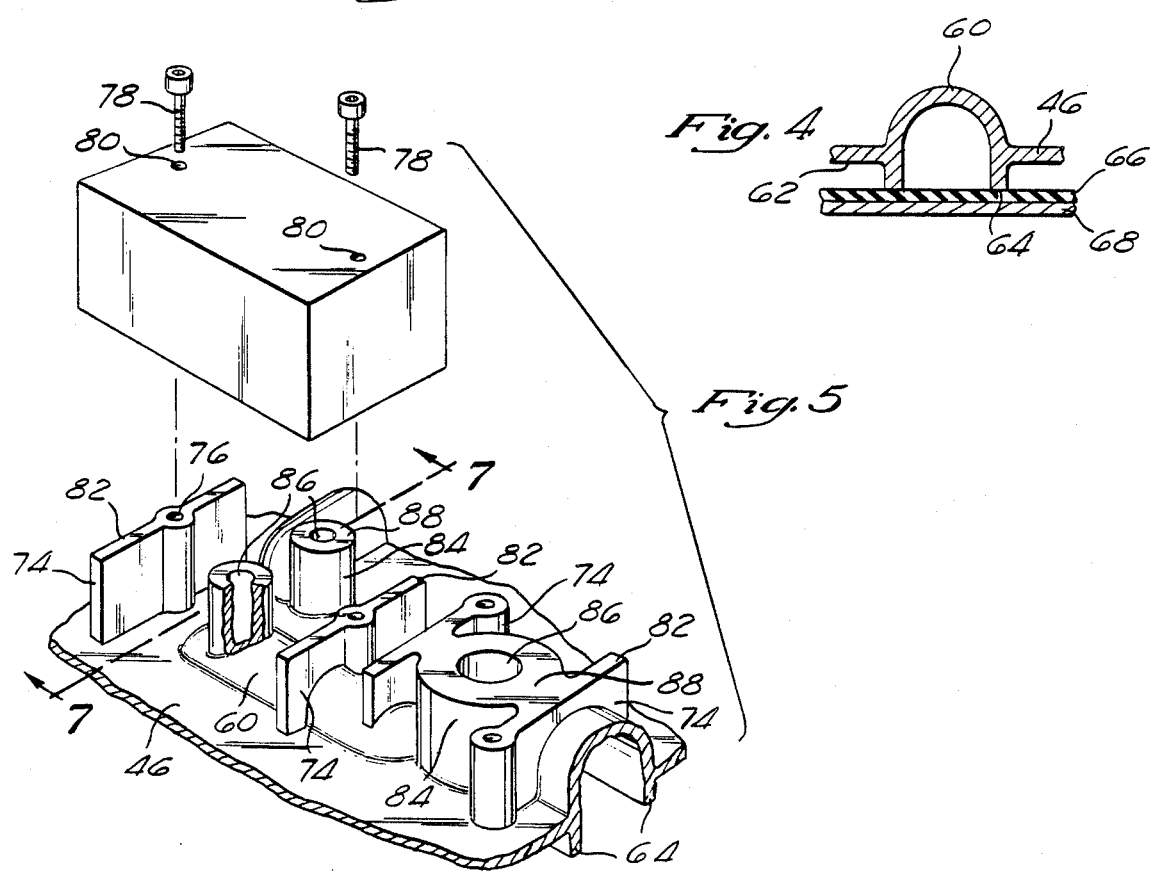

VENTILATOR MANIFOLD

BACKGROUND OF THE INVENTION

This invention relates generally to the field of medical ventilators, and more particularly to a ventilator having a manifold on which the pneumatic components of the ventilator are mounted.

Medical ventilators have been developed to provide artificial respiration to patients whose breathing ability is impaired. Typically, a ventilator will deliver a breath to the patient from a pressurized source of gas. A gas storage chamber, called an accumulator, is usually provided on the ventilator to store a supply of gas for use when the demand by the patient exceeds the flow rate of the source. Pressurized gas flowing from the accumulator is brought down to a lower, constant pressure level by a regulator. Flow to the patient during inspiration is governed by a flow control valve, which is downstream of the regulator. When the flow control valve opens, pressurized gas is introduced to the patient's lungs. After the flow control valve closes, ending the inspiration phase of the breath, the patient's respiratory gases are vented to the atmosphere through an exhalation valve, which opens after respiration is completed and closes before the next inspiration phase begins.

Previous ventilators have had microcomputer controllers to enable the ventilator to operate in several modes so that the degree of support that the ventilator provides to the patient's natural breathing patterns can be varied. At one extreme, the ventilator can provide fully controlled ventilation in which the ventilator has complete control over when the breath is delivered and the volume of gases received by teh patient during each breath. In the fully controlled mode, all of the flow parameters are preset by an operator in accordance with the particular needs of the patient.

At the other extreme, the ventilator can be programmed to permit "spontaneous" breathing by the patient. During the spontaneous breathing mode, the breath rate, the volume of gas inhaled during each breath, and other flow parameters are not predetermined. The inspiration and expiration phases of each breath are commenced in response to efforts by the patient. In between the "volume control" and the "spontaneous breath" modes, various degrees of ventilator supported respiration are available.

To promote the portability of the ventilator, all of the pneumatic and electrical components of the ventilator must be mounted on a stable base, which is typically formed by a sheet metal chassis. The components are secured to the chassis by means of separate mounting brackets. To establish fluid communication between the various pneumatic components, previous ventilators have utilized flexible tubing which is manually joined to the respective inlets and outlets of the components.

A major drawback to previous ventilators of this type has been that due to the large quantities of tubing required to interconnect the various components, a complex arrangement of intertwined tubing is created. As a result, the ventilator is difficult to assemble and service. Additionally, in order to have sufficient access to mount the components on the base with the brackets, and to connect the tubing, the overall size of the ventilator is quite large. Consequently, the ventilator occupies a large amount of the scarce space surrounding a hospital bed in an intensive care unit.

Thus, a need exists for a ventilator which mounts the components and establishes fluid communication between the components in a manner which enables the ventilator to be compact, inexpensive, and easy to assemble and repair.

SUMMARY OF THE INVENTION

The present invention is a ventilator having a manifold which is compared of a base on which a plurality of pneumatic components are mounted. A plurality of ducts extend through the base to permit fluid communication between the pneumatic components. Advantageously, the ducts are formed as part of the base, and thus the need for tubing to interconnect the pneumatic components is eliminated. This enables the components to be mounted very closely together since space for tubing need not be provided. As a result, the overall size of the ventilator can be minimized.

The manifold is preferably formed as a one-piece metal casting. The ducts are pratly exposed so as to facilitate the formation of the manifold from a molding or casting process with a minimun of machining. Means are provided for removably sealing the ducts from the atmosphere so as to permit access to the ducts for maintenance and repair.

In one preferred embodiment, at least one pneumatic component is formed as a part of the manifold. In particular, this component is a gas storage chamber, such as an accumulator. Further, the manifold may be formed with a plurality of fins which act as a heat sink for the heat generating electronics of the ventilator. By incorporating these components directly into the manifold, assembly of the ventilator is greatly simplified. Further, the cost of the ventilator is reduced due to the fewer number of parts required to assemble the ventilator.

Advantageously, the casting incorporates means for mounting the pneumatic components to the base. Preferably, the pneumatic components are secured to a plurality of mounting blocks which are formed on the base. Threaded bores are provided within the mounting blocks to receive threaded fasteners. The mounting blocks beneficially eliminate the need for separate mounting brackets, which simplifies the ventilator construction and permits further reductions in the size of the ventilator.

To establish fluid communication between the pneumatic components and the ducts, a plurality of stubs extend upwardly from the base. Each stub has an access port therein which feeds into a duct. The pneumatic components are designed so that when they are secured to the mounting blocks, their respective inlets and outlets will be aligned with and sealed to the access ports. Thus, fluid communication between the various components is established by simply securing the components to the base so that the components engage the stubs.

BRIEF DESCRIPTION OF THE DRAWINGS

FIG. 3 is a bottom plan view of the manifold shown in FIG. 2.

FIG. 4 is a cross-sectional view of the manifold in FIG. 3, taken along line 4—4.

FIG. 5 is an enlarged exploded perspective view of a portion of the manifold and a flow control valve which is mounted thereon.

DETAILED DESCRIPTION OF A PREFERRED EMBODIMENT

Figure 1:
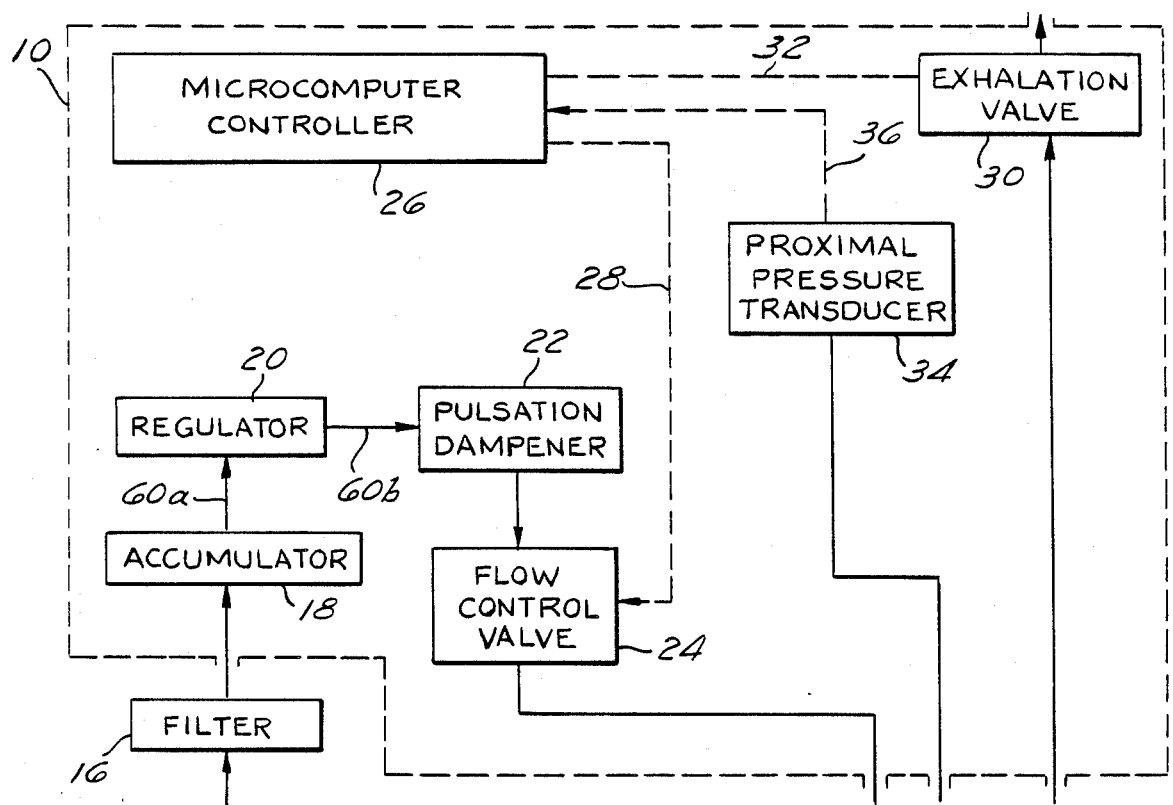
FIG. 1 is a schematic view of the pneumatic layout of the ventilator according to one embodiment of the present invention.

Referring to FIG. 1, the present ventilator is shown schematically at 10. The ventilator 10 receives pressurized gas, such as air or an oxygen blend, from a source 12 and controls the flow of gas to a patient 14 so as to provide artificial respiration. As will be apparent to those skilled in the art, the schematic of FIG. 1 has been simplified by the elimination of various commonly used elements such as check valves, safety valves, pressure gauges, etc.

A description of the components illustrated in FIG. 1, and their operation, will be understood from the following description of the flow path of gas through the ventilator 10. The gas initially passes from the source 12 through a coalescing filter 16, so as to remove both liquids and solids from the gas stream. After being filtered, the gas enters an accumulator 18, which is a rigid chamber for the temporary storage of the pressurized gas. The accumulator 18 acts as a reservoir from which gas is drawn during periods of peak demand, such as during inspiration by the patient 14. Downstream of the accumulator 18, a pneumatic regulator 20 is positioned. Gas flowing from the regulator 20 is maintained at a constant pressure of approximately 20 psig, which is referred to herein as the "system pressure."

System pressure gas enters a pulsation dampener 22 which, like the accumulator 18 is a rigid gas storage chamber. However, the volume of the pulsation dampener 22 is smaller than that of the accumulator 18, and the gas in the pulsation dampener 22 is at the system pressure. The pulsation dampener 22 serves to damp out pressure changes caused by transient flow conditions so as to maintain pressure downstream of the regulator 20 at a constant 20 psig.

The pulsation dampener 22 feeds gas to a flow control valve 24. The flow control valve 24 regulates the flow rate of gas which is delivered to the patient 14 during inspiration. The flow control valve 24 can assume a plurality of positions, so as to permit various flow rates of gas to the patient 14. The position of the flow control valve 24 is controlled by a microcomputer controller 26. An electronic signal 28 is sent by the controller 26 to cause opening or closing of the valve 24.

The patient 14 is fitted with an endotracheal tube 29 which establishes fluid communication between the patient's lungs and the ventilator 10. As is well known, the endotracheal tube is inserted in the patient's trachea or wind pipe, and is surrounded by a balloon which forms a seal with the trachea so that all gas flow into and out of the lungs takes place through the endotracheal tube, which is in fluid communication with the ventilator 10.

An exhalation valve 30 is provided to establish fluid communication between the patient's lungs and the atmosphere. When open, the exhalation valve 30 permits the patient 14 to exhale by venting respiratory gases to the atmosphere through the endotracheal tube. Opening and closing of the exhalation valve 30 is governed by the controller 26, which sends an electrical signal 32 to the exhalation valve 30 to effect a change in the position of the exhalation valve 30. The controller 26 determines the proper position of the exhalation valve 30 based on feedback from a proximal pressure transducer 34. The proximal pressure transducer 34 measures the pressure of the gas on the ventilator side of the seal formed by the endotracheal tube, which is referred to as the "proximal" gas. Feedback to the controller 26 is in the form of an input signal 36 from the proximal pressure transducer 34, which is an electrical analog of the proximal pressure.

When the ventilator 10 is operating in a fully controlled mode, in which the patient 14 has no control over the flow parameters, inspiration begins when the flow control valve 24 is signalled to open by the controller 26. Opening of the flow control valve 24 causes gas to enter the patient's lungs through the endotracheal tube. The exhalation valve 30 remains closed during inspiration so that the gas in the endotracheal tube does not leak to the atmosphere. When the flow control valve 24 closes on command from the controller 26, the inspiration phase of the breath terminates.

The expiration phase is commenced by the opening of the exhalation valve 30, the timing of which is determined by the controller 26. Upon opening of the exhalation valve 30, gas within the patient's lungs is automatically expelled to the atmosphere.

The ventilator 10 includes a positive expiration end pressure (PEEP) feature so that an operator can preset what the pressure level of the proximal gases should be at the end of each breath. During expiration, the controller 26 compare the actual proximal pressure to the predetermined pressure level (PEEP) and when the proximal pressure reaches the predetermined level, the controller 26 sends a signal 32 to cause the valve 30 to approach the closed position. The controller 26 then "servos", or controls the position of the valve 30 on a closed loop basis so as to maintain the actual proximal pressure equal to the predetermined pressure. After the exhalation valve 30 is completed closed, the flow control valve 24 opens to end the expiration phase and begin the inspiration phase again. This cycle is repeated continuously to establish artificial respiration.

Figure 6:
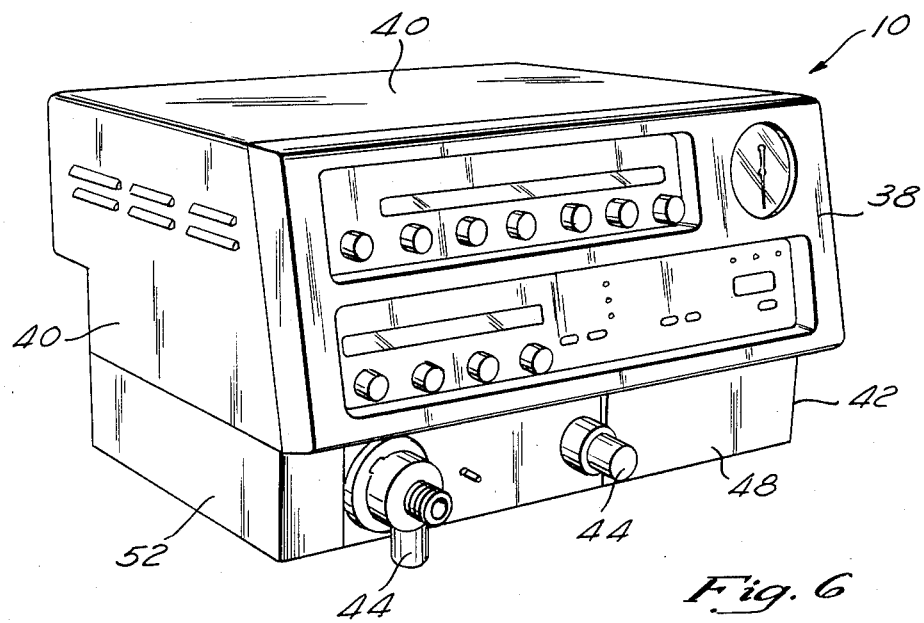
FIG. 6 is a perspective view of the fully assembled ventilator.

Turning now to FIG. 6, the exterior appearance of the assembled ventilator 10 is shown. At the front of the ventilator 10, a control panel 38 is provided. Various knobs and switches on the control panel 38 are manipulated by an operator to establish predetermined flow parameters during the operation of the ventilator 10. Enclosing the top and sides of the ventilator 10 is a sheet metal cover 40 which is removable to allow access to the various electrical and pneumatic components within the ventilator 10. The control panel 38 and cover 40 rest on a manifold 42 which forms the lower portion of the ventilator 10. The manifold 42 is generally rectangular in outline when viewed from above. All of the pneumatic and electrical components of the ventilator 10 are secured directly to the manifold 42. Fittings 44 extend through the manifold 42 to receive gas from the source 12 and to establish fluid communication with the patient 14.

Figure 2:
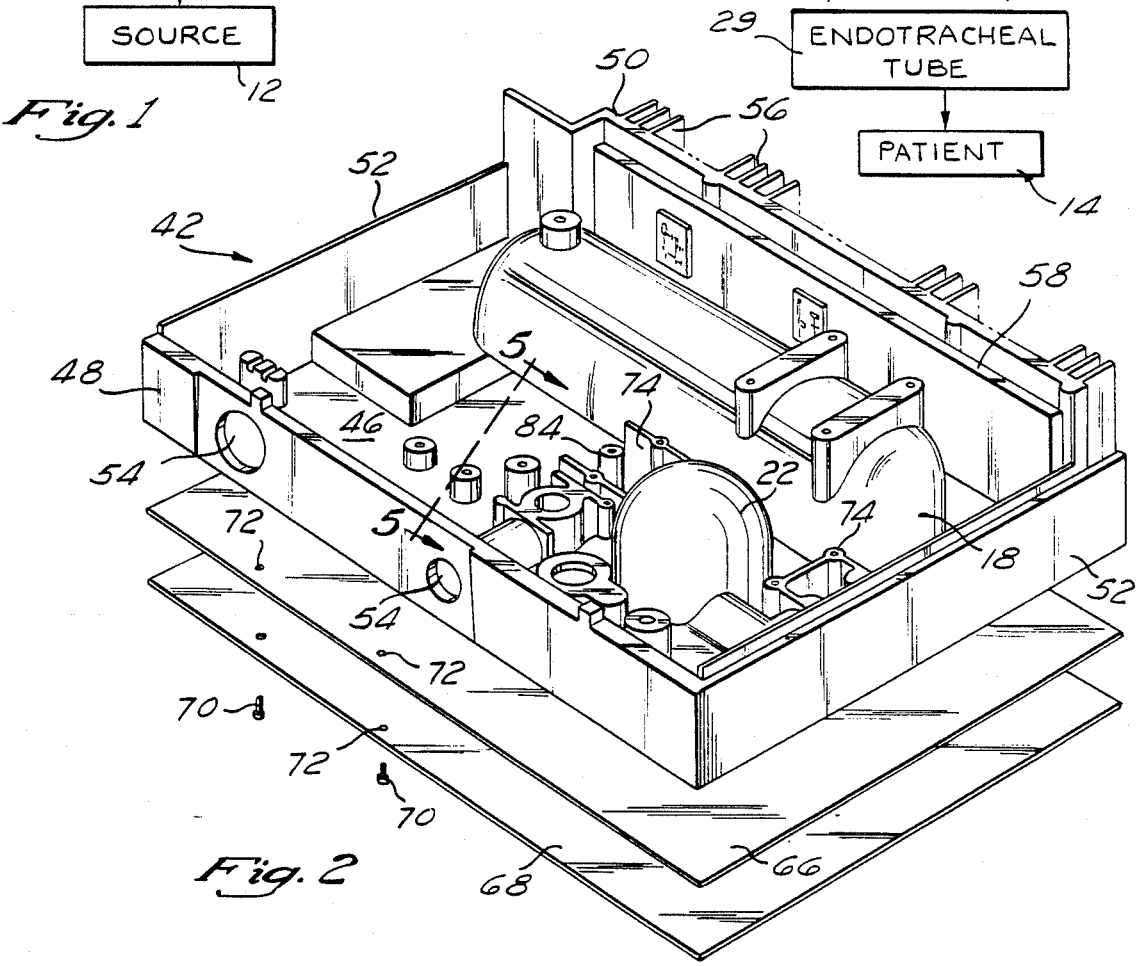
FIG. 2 is an exploded perspective view of the present manifold, gasket, and sealing plate.

FIGS. 2 and 6 show the manifold 42 with most attachments, such as the control panel 38, cover plate 40, and the pneumatic components removed for clarity. The manifold 42 is formed as a one-piece aluminum casting and has a generally horizontal, planar base 46 which is surrounded on all four sides by a vertically upright front wall 48, a rear wall 50, and a pair of side walls 52. Holes 54 are cut through the front wall 48 to allow for passage of the fittings 44 shown in FIG. 6. The control panel 38 is mounted on the top of the front wall 48, while the cover 40 rests on top of both side walls 52.

Referring to FIG. 2, protruding outwardly from the rear wall 50 are a plurality of planar, vertically oriented, parallel fins 56. On the interior side of the rear wall 50, a printed circuit board 58 is secured. The various electrical components mounted on the circuit board 58 in part form the microcomputer controller 26. The fins 56, which have a large surface area, act as a heat sink for the heat generating components on the printed circuit board 58. The fins 56 are formed integrally with the manifold 42, that is, the fins 56 are formed as a part of the manifold casting and need not be separately fabricated and secured to the manifold 42.

Several of the pneumatic components of the ventilator 10 are also formed integrally with the manifold 42, or as a part of the one-piece manifold 42. In particular, an elongated, hollow gas chamber extends upwardly from the base 46 to form the accumulator 18. The walls of the accumulator 18 are rigid, and when viewed in cross section through a plane which is perpendicular to the longitudinal axis of the accumulator 18 and to the base 46, have an inverted U-shape. Likewise, the pulsation dampener 22 is a hollow, rigid gas storage chamber which extends upwardly from the base 46 and is formed as part of the manifold. The pulsation dampener 22 has a substantially circular outline when viewed from above, and also has an inverted U-shaped cross section when viewed through a plane which runs through the concentric axis of the dampener 22 and perpendicularly to the base 46.

Fluid communication between the components mounted on the manifold 42 is achieved through a network of ducts 60 which are formed in the base 46, as is best seen in FIGS. 3, 4, and 5. As shown in FIG. 4, the ducts 60 have a substantially inverted U-shape when viewed in cross section. The ducts 60 replace almost all uses of tubing to interconnect the pneumatic components, although in the preferred embodiment of the present ventilator 10 certain fluid connections are still established by means of tubing (not shown). Each of the ducts 60 correspond to the schematic lines of flow shown in FIG. 1. For example, flow between the accumulator 18 and regulator 20 is established by a duct 60a, which begins at the accumulator 18 and terminates where the regulator 20 is mounted, as indicated by the flow line 60a in FIG. 1. Further, a duct 60b extends from the regulator 20 to the pulsation dampener 22, corresponding to the flow line numbered 60b in FIG. 1.

The ducts 60, the accumulator 18 and the pulsation dampener 22 are exposed on an underside 62 of the base 46. The walls of the ducts 60, pulsation dampener 22 and accumulator extend beneath the plane of the underside 62 of the base 46 and terminate in flat edges 64. To seal the ducts, the pulsation dampener 22 and the accumulator 18 from the atmosphere, a substantially rectangular, planar, resilient gasket 66 which conforms in shape to the outline of the base 46 is pressed into sealing engagement with the edges 64. To maintain the gasket 66 in sealing engagement with the edges 64, a rigid, planar, sealing plate 68, having the same shape as the gasket 66 is secured to the manifold 42 so as to sandwich the gasket 66 between the edges 64 and the sealing plate 68. As shown in FIGS. 2 and 4, the sealing plate 68 and the gasket 66 are removably secured to the underside 62 of the base 46 by means of screws 70 which pass through aligned holes 72 in the gasket 66 and sealing plate 68 and are threaded into the base 46. Access to the ducts 60, pulsation dampener 22, and accumulator 18 for repair can be easily had by removing the sealing plate 68 and gasket 66.

As shown in FIGS. 2 and 5, a plurality of integrally-formed mounting blocks 74 extend upwardly from the base 46. A threaded bore 76 extends vertically downward into each mounting block 74. The various pneumatic components, such as the flow control valve 24, are removably secured to the base 46 by threading a bolt 78 through a hole 80 in the housing of the flow control valve 24 (shown schematically) and into the bore 76 in the mounting block 74. When assembled, the flow control valve 24 rests directly on a top surface 82 of the mounting blocks 74.

Figure 7:
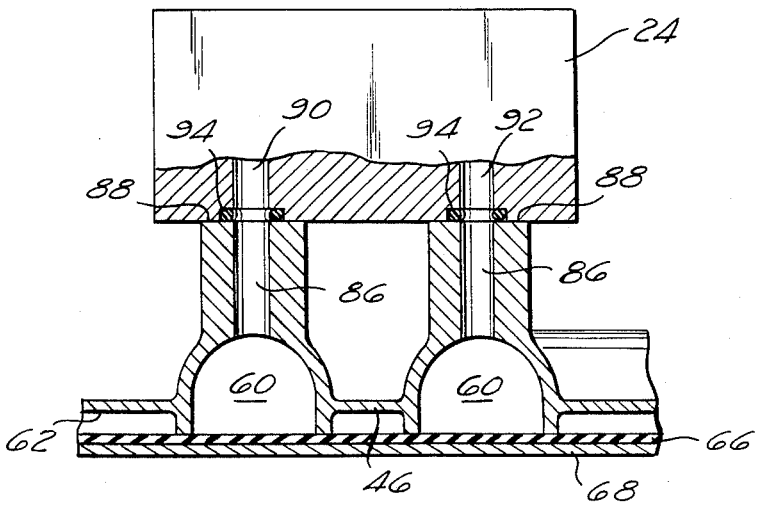
FIG. 7 is a cross-sectional view of the flow control valve shown in FIG. 5, as mounted on the manifold.

To establish fluid communication between the various pneumatic components and the corresponding ducts 60, a plurality of integrally formed stubs 84 extend vertically upwardly from the base 46 from points along the ducts 60. As is shown in FIG. 7, the stubs 84 are cylindrical in shape, and have a central vertical bore or access port 86 therein which extends from a top surface 88 of the stubs 84 through to the ducts 60.

The flow control valve 24, like other pneumatic components which are not shown, has an inlet 90 and an outlet 92 which align with the access ports 86 when the flow control valve 24 is secured to the appropriate mounting blocks 74. The flow control valve 24 rests directly on the top surface 88 of the stubs 84, which is level with the top surfaces 82 of the mounting blocks 74. Resilient annular washers 94 suround the inlet 90 and outlet 92 of the flow control valve 24 so that a seal is formed between the flow control valve 24 and the access port 86.

As will be apparent from the foregoing, the production of the manifold 42 is greatly facilitated by its design. The manifold 42 may be formed as a single piece by either casting or molding. Since the ducts 60 are exposed on the underside 62 of the base 46, it is easy to form the ducts 60 during casting, as opposed to drilling or boring the ducts 60 after the casting is complete. After casting, the machining of the manifold 42 is minimal. For example, the duct edges 64, the stub top surfaces 88 and the mounting block top surfaces 88 must be milled so that all of the surfaces are level and smooth enough to form good seals. Additionally, the access ports 86 in the stubs 84 must be drilled and the threaded bores 76 in the mounting blocks must be drilled and tapped.

The pneumatic components are quickly and easily secured to the manifold 46 since the only mounting hardware required that is not part of the manifold are the bolts 78. Fluid connections between the components are, in almost all cases, established automatically through the access ports 86 and ducts 60 upon securing the components to the mounting blocks 74. In the case of the integral components such as the fins 56, accumulator 18, and pulsation dampener 22, no assembly is required at all.

I claim:

1. A ventilator which provides artificial respiration to a patient from a source of pressurized gas, said ventilator comprising:

a flow control valve means for controlling the flow of inspiratory gas to said patient from said source of pressurized gas;

means for establishing gas flow into and out of said patient's airway, said flow establishing means being in fluid communication with said flow control valve means;

an exhalation valve means for controlling the flow of gas from said patient to the atmosphere, said exhalation valve means in fluid communication with said flow establishing means;

a manifold having a top side and an underside, said flow control valve means and said exhalation valve means mounted on said top side of said manifold;

mounting surfaces formed on said top side of said manifold, said flow control and exhalation valve means being supported by said mounting surfaces when mounted on said manifold;

a plurality of integral ducts formed in said manifold, said ducts permitting fluid communication between said source of pressurized gas and said patient through said manifold;

a plurality of access ports extending through said top side of said manifold and into said ducts, said access ports positioned on said manifold so as to permit fluid communication between said flow control and exhalation valve means and said ducts when said flow control and exhalation valve means are mounted on said manifold;

an inlet fitting mounted on said manifold, said inlet fitting in fluid communication with said source of pressurized gas, a first one of said ducts establishing fluid communication between said inlet fitting and said flow control valve means, wherein substantially the entire length of said duct is exposed to the atmosphere along the underside of said manifold;

a patient fitting mounted on said manifold, said patient fitting establishing fluid communication between said flow establishing means and a second duct extending between said flow control valve means and said patient fitting, wherein substantially the entire length of said second duct is exposed to the atmosphere along the underside of said manifold;

a gasket which sealingly engages the underside of said manifold so as to seal said ducts from the atmosphere;

a sealing plate which forces said gasket into sealing engagement with said manifold, said gasket being sandwiched between said sealing plate and said manifold, said gasket and said sealing plate combining to form a wall enclosing said ducts; and wherein the exposed structure of said ducts permits the formation of said manifold, complete with said integral ducts, through a molding or casting process.

2. The ventilator of claim 1, wherein said manifold has a one-piece construction.

3. The ventilator of claim 2, wherein said manifold is formed from cast metal.

4. The ventilator of claim 1, wherein said ducts have a longitudinal axis and a substantially inverted U-shape when viewed in cross section through a plane which is perpendicular to the longitudinal axis of each of said ducts.

5. The ventilator of claim 1, wherein said gasket and said sealing plate are substantially planar and oriented substantially parallel to the longitudinal axes of said ducts.

6. The ventilator of claim 1, wherein said manifold further comprises at least one pneumatic component formed integrally with said manifold.

7. The ventilator of claim 6, wherein said pneumatic component comprises a gas storage chamber.

8. The ventilator of claim 7, wherein said gas storage chamber is positioned downstream of said inlet fitting and upstream of said flow control valve means, said first duct establishing fluid communication between said inlet fitting and said gas storage chamber, and between said gas storage chamber and said flow control valve means.

9. The ventilator of claim 7, wherein said gas storage chamber is exposed on the underside of said manifold, and wherein said gasket and sealing plate seal said gas storage chamber from the atmosphere.

10. The ventilator of claim 1, wherein said sealing plate and gasket are removably secured to said manifold.

11. The ventilator of claim 1, wherein said flow establishing means comprises an endotracheal tube.

12. The ventilator of claim 1, further comprising a plurality of stubs formed in said manifold and extending upwardly therefrom, said access ports extending through said stubs, said flow control and exhalation valve means respectively being mounted on said manifold so as to sealingly engage said stubs and be in fluid communication with said ducts through said access ports, without requiring a coupling or fitting to join each of said access ports and said flow control and exhalation valve means.

13. The ventilator of claim 12, wherein said stubs terminate in substantially planar top surfaces, said flow control valve means sealingly engaging said top surfaces, said flow control valve means having inlet and outlet passageways which are respectively aligned with said access ports.

14. The ventilator of claim 1, wherein said ventilator further comprises a plurality of mounting blocks formed on said manifold and extending upwardly therefrom, and wherein said mounting surfaces comprise substantially planar top surfaces on said mounting blocks, said flow control and exhalation valve means resting directly on said mounting block top surfaces.

15. The ventilator of claim 14, wherein said mounting blocks include threaded bores therein so that said flow control and exhalation valve means can be removably secured to said mounting blocks by means of threaded fasteners.

16. A ventilator which provides artificial respiration to a patient from a source of pressurized gas, said ventilator comprising:

a flow control valve means for controlling the flow of inspiratory gas to said patient from said source of pressurized gas;

means for establishing gas flow into and out of said patient's airway, said flow establishing means being in fluid communication with said flow control valve means;

a manifold having a top side and an underside, said flow control valve means being mounted on said manifold;

a plurality of integral ducts formed in said manifold, said ducts permitting fluid communication between said source of pressurized gas and said patient through said manifold;

a plurality of access ports extending through said top side of said manifold and into said ducts, said access ports positioned on said manifold so as to permit fluid communication between said valve means and said ducts when said valve means is mounted on said manifold;

a gas storage chamber integral with said manifold, said gas storage chamber being positioned between and in fluid communication with both said source of pressurized gas and said flow control valve means;

an inlet fitting mounted on said manifold, said inlet fitting in fluid communication with said source of pressurized gas, a first one of said ducts establishing fluid communication between said inlet fitting and said gas storage chamber, wherein substantially the entire length of said duct is exposed to the atmosphere along the underside of said manifold;

a second duct establishing fluid communication between said gas storage chamber and said flow control valve means, wherein substantially the entire length of said second duct is exposed to the atmosphere along the underside of said manifold;

a patient fitting mounted on said manifold, said patient fitting in fluid communication with said flow establishing means and a third duct, said third duct establishing fluid communication between said flow control valve means and said patient fitting, wherein substantially the entire length of said third duct is exposed to the atmosphere along the underside of said manifold;

means for sealingly engaging the underside of said manifold so as to form a wall enclosing said ducts and said gas storage chamber and seal said ducts and said gas storage chamber from the atmosphere; and wherein the exposed structure of said ducts and said gas storage chamber permits the formation of said manifold, complete with said integral ducts and said integral gas storage chamber, through a molding or casting process.

17. The ventilator of claim 16, wherein said manifold has a one-piece construction.

18. The ventilator of claim 17, wherein said manifold is formed from cast metal.

19. The ventilator of claim 16, wherein said manifold further comprises:

means for mounting a printed circuit board; and a plurality of fins integrally formed in said manifold, said fins forming a heat sink for said printed circuit board.

20. The ventilator of claim 16, wherein said flow establishing means comprises an endotracheal tube.

21. The ventilator of claim 16, wherein said sealing means comprises:

a gasket which sealingly engages the underside of said manifold; and a sealing plate which forces said gasket into sealing engagement with said manifold, said gasket being sandwiched between said sealing plate and said manifold, said sealing plate and said gasket cooperating to form a wall enclosing said ducts and said gas storage chamber and seal said ducts and gas storage chamber from the atmosphere.

22. The ventilator of claim 21, wherein said gasket and said sealing plate are removably secured to said manifold.

* * * * *